United States Patent [19]
Yoon et al.

[11] Patent Number: 5,903,622
[45] Date of Patent: May 11, 1999

[54] ACCELERATOR-BASED NEUTRON SOURCE FOR BORON NEUTRON CAPTURE THERAPY (BNCT) AND METHOD

[75] Inventors: Woo Y. Yoon; James L. Jones; David W. Nigg; Yale D. Harker, all of Idaho Falls, Id.

[73] Assignee: Lockheed Martin Idaho Technologies Company, Idaho Falls, Id.

[21] Appl. No.: 08/713,317

[22] Filed: Sep. 13, 1996

Related U.S. Application Data

[63] Continuation-in-part of application No. 08/237,504, May 3, 1994, abandoned.

[51] Int. Cl.[6] .............................. G21H 5/00; G21G 1/10
[52] U.S. Cl. ...................... 376/156; 376/110; 376/159; 376/458
[58] Field of Search ................... 376/156, 157, 376/159, 110, 200, 195–198, 458

[56] References Cited

U.S. PATENT DOCUMENTS

| | | | |
|---|---|---|---|
| 2,868,987 | 1/1959 | Salsig, Jr. et al. ........................ | 376/156 |
| 2,902,613 | 9/1959 | Baldwin et al. .......................... | 376/156 |
| 2,933,442 | 4/1960 | Lawrence et al. ....................... | 376/200 |
| 3,833,814 | 9/1974 | Nablo ...................................... | 376/105 |
| 4,251,726 | 2/1981 | Alvarez ................................... | 376/157 |
| 4,381,280 | 4/1983 | Roberts ................................... | 376/105 |
| 4,666,651 | 5/1987 | Barjon et al. ............................ | 376/151 |
| 4,756,866 | 7/1988 | Alvarez ................................... | 376/157 |
| 5,392,319 | 2/1995 | Eggers .................................... | 376/151 |

OTHER PUBLICATIONS

Neutron Beam Design, Development, and Performance for Neutron Capture Therapy, Plenum Press, N.Y. (1990), pp. 83–95, article by Wheeler et al.

Nuclear Technology, vol. 55, (Dec. 1981), pp. 642–655, Oka et al.

Int. J. Appl. Radiat. Isot., vol. 24 (1973), pp. 124–126, Lindner et al (I).

Advances in Neutron Capture Therapy, Plenum Press N.Y., (1993) pp. 85–88, article by Rief et al.

(List continued on next page.)

*Primary Examiner*—Harvey E. Behrend
*Attorney, Agent, or Firm*—Alan D. Kirsch

[57] ABSTRACT

A source for boron neutron capture therapy (BNCT) comprises a body of photoneutron emitter that includes heavy water and is closely surrounded in heat-imparting relationship by target material; one or more electron linear accelerators for supplying electron radiation having energy of substantially 2 to 10 MeV and for impinging such radiation on the target material, whereby photoneutrons are produced and heat is absorbed from the target material by the body of photoneutron emitter. The heavy water is circulated through a cooling arrangement to remove heat. A tank, desirably cylindrical or spherical, contains the heavy water, and a desired number of the electron accelerators circumferentially surround the tank and the target material as preferably made up of thin plates of metallic tungsten. Neutrons generated within the tank are passed through a surrounding region containing neutron filtering and moderating materials and through neutron delimiting structure to produce a beam or beams of epithermal neutrons normally having a minimum flux intensity level of $1.0 \times 10^9$ neutrons per square centimeter per second. Such beam or beams of epithermal neutrons are passed through gamma ray attenuating material to provide the required epithermal neutrons for BNCT use.

5 Claims, 3 Drawing Sheets

OTHER PUBLICATIONS

Neutron Beam Design, Development, and Performance for Neutron Capture Therapy, Plenum Press, N.Y. (1990), pp. 235–245, article by Becker et al.

Progress in Neutron Capture Therapy for Cancer, Plenum Press N.Y. (1992), pp. 53–56, article by Choi et al.

Strahlentherapie und Onkologie, vol. 165, (1989), pp. 87–90, Less et al.

Neutron Beam Design, Development, and Performance for Neutron Capture Therapy, Plenum Press, N.Y. (1990), pp. 97–107, Harrington.

Nuc. Inst. and Methods, vol. 119, No. 2, (Jul. 1974), pp. 217–227, Harling.

Int. J. Appl. Radiat. Isot., vol. 24 (1973), pp. 121–124, Lindner et al.

Jones, et al, *Feasibility Study of the Application of a Linear Electron Accelerator to BNCT,* Abstracts for the Twelfth International Conference on the Application of Accelerators in Research & Industry, Nov. 2–5, 1992, p. 59.

Nigg, et al, *Conceptual Physics Design of an Epithermal–Neutron Facility for Neutron Capture Therapy at the GeorgieaTech Research Reactor,* Neutron Capture Therapy–I, pp. 146–147.

Auterinen et al, pp. 81–84, "Advances in Neutron Capture Therapy", Ed. Soloway et al, Plenum Press, N.Y. 1993.

ACCELERATOR-BASED NEUTRON SOURCE FOR BORON NEUTRON CAPTURE THERAPY (BNCT) AND METHOD

PRIORITY

This is a continuation-in-part of a similarly-entitled, U.S. patent application Ser. No. 08/237,504 filed May 3, 1994, abandoned as of the filing date of the present application.

CONTRACTUAL ORIGIN OF THE INVENTION

The United States Government has rights in this invention pursuant to Contract No. DE-AC07-94ID13223 between the United States Department of Energy and Lockheed-Martin Idaho Technologies, Inc.

BACKGROUND OF THE INVENTION

1. Field

The invention is in the medical field of radiation oncology, specifically boron neutron capture therapy for cancer, usually spoken of as BNCT. It is concerned with accelerator-based apparatus for, and with methods of, producing epithermal neutron spectra for application to humans and to animals in general.

2. State of the Art

BNCT is a still experimental, therapeutic, binary modality for treatment of certain types of refractory malignancies. The current area of research interest is Glioblastoma Multiforme, a primary brain tumor. Procedurally, boron-10, which has a particularly large cross section for capture of "thermal" neutrons, i.e., neutrons having energies less than 0.5 electron volts (eV), is preferentially introduced into the malignant tissue by administration of a suitable boronated pharmaceutical. A thermal neutron field is then generated within such tissue by application thereto of an externally-produced neutron beam, the objective being the selective destruction of the malignant tissue by energetic, secondary, charged particles, specifically helium-4 and lithium-7 ions, that result from neutron capture interactions in the boron-10. The average total energy of such ions is 2.35 million electron volts (MeV). This energy is deposited along charged particle paths that are comparable in dimensions to the cellular dimensions of the malignant tissue, thereby offering the possibility of cancer cell inactivation with only limited damage to nearby healthy tissue, which, ideally, contains no boron.

Until recently, human applications of BNCT were limited to some early (in the 1950s) trials in the United States and more recently to an extensive series of treatments conducted over a period of approximately the last twenty years in Japan. The early trials in the U.S. were unsuccessful for a variety of reasons. The more recent applications of BNCT in Japan have been much more successful, primarily because of the development and use of better boronated pharmaceuticals. This has led to a worldwide resurgence of interest in BNCT research, and to the resumption, in 1994 of clinical trials in the USA.

Most BNCT research efforts have been strongly influenced by the recognition that an "epithermal" neutron beam (a beam comprised primarily of neutrons whose energies fall within the energy range between 0.5 and 10,000 eV) should ultimately prove to be optimal for human clinical applications. Such a beam will have an advantage over the relatively low energy, "thermal" neutron beams currently used in Japan for application to human brain tumors. This realization is a result of the known physical fact that "epithermal" neutrons will penetrate a few centimeters into tissue before forming a neutron flux peak, whereas "thermal" neutrons do not have nearly as much penetrating power. Thus, if a beam of epithermal neutrons can be produced that is not, in itself, capable of causing significant biological damage, it will offer a safe and effective way of applying BNCT for deep-seated malignancies.

So far, however, only nuclear reactors have produced epithermal neutron beams useful for BNCT. Neutrons leaking out of one side of an active reactor core are directed into and through a filtering (allowing neutrons of a certain energy range to pass through) and moderating (reducing energy of all neutrons to a lower average level) region containing materials that cause, via neutron scattering and absorption, the so-derived, very high energy neutron beam to assume a spectrum whose energy distribution is strongly peaked in the desired epithermal energy range. The epithermal neutron beam that emerges from the filtering and moderating region is passed through gamma ray shielding material before application.

Materials which have proven suitable for use in the filtering and moderating region of nuclear-reactor-based, epithermal neutron facilities for BNCT are various combinations of metallic aluminum, heavy water ($D_2O$), sulfur, aluminum trifluoride ($AlF_3$), alumina ($Al_2O_3$), titanium, and vanadium, as well as a mixture of metallic aluminum and the material Teflon®. Gamma shielding materials that have been used are lead, bismuth, and liquid argon.

Epithermal neutron beams that have been produced by reactor-based facilities have epithermal neutron flux intensities in the range of $2.0 \times 10^8$ neutrons per square centimeter per second ($n/cm^2/s$) to $1.0 \times 10^{10}$ $n/cm^2/s$.

It has been recognized that an epithermal neutron beam for BNCT use should have any neutron flux intensity above 10,000 eV suppressed to a level that is roughly two orders of magnitude (factors of 10) below the intensity of the flux in the useful epithermal energy range. This serves to protect a patient from normal tissue damage caused by non-selective, proton-recoil interactions that occur in hydrogenous tissue when such tissue is exposed to neutron radiation. Also, it has been recognized that proton recoil interactions are non-selective and that such interactions induced by neutrons having energies significantly above the upper cutoff of the epithermal energy range are particularly damaging to normal tissue and should be minimized to the extent possible by careful neutron beam design to suppress the high-energy spectral component. Also, it has been recognized as important to suppress any "thermal" neutron component of an epithermal neutron beam, since it can cause significant surface tissue damage. "Thermal" neutrons are generally suppressed in reactor-based, epithermal neutron beams by inclusion of small amounts of cadmium, lithium, and boron in various locations within and around the epithermal neutron filtering regions.

Some nuclear-reactor-based, epithermal neutron beam facilities have been constructed and are in operation. It is expected that these facilities will continue to be used extensively in BNCT research and probably for initial human clinical trials of epithermal neutron BNCT in the United States. However, there has also been a great deal of interest in the development of a practical accelerator-based source of epithermal neutrons for BNCT. Particle accelerators are already used routinely for various other types of cancer radiotherapy and are a well-accepted technology in the clinical medicine community. Designs for accelerator-based neutron sources for BNCT that feature the use of proton beams impinging on either lithium or beryllium targets have been proposed in the literature and, in some cases, low-intensity prototypes have been constructed. In these concepts, protons having energies of approximately 2.5 MeV induce neutron-producing interactions in target materials. The resultant neutrons are then filtered and moderated into the desirable epithermal energy range using materials and techniques that are to some extent similar to those employed to produce reactor-based epithermal neutron beams. These proton devices have, however, proven to be difficult to scale to the output neutron beam intensities necessary for clinical application of BNCT. Because of problems associated with production of a proton beam of sufficient intensity and with removing the rather high level (50–250 kilowatts) of waste heat that is generated within the accelerator target, a sufficiently intense accelerator-based source of epithermal neutrons that are of practical utility for BNCT has yet to be constructed.

It has been well-known for years that neutrons can also be produced using a particle accelerator via a two-stage process by which an electron beam of sufficient energy is directed upon a target material having a relatively high atomic number (e.g. tungsten), and the bremsstrahlung photon radiation thus produced is directed into a material or a combination of materials that exhibit a high cross section for photoneutron production. Such a particle accelerator has been used to produce neutrons for a variety of non-medical purposes. In such applications, however, relatively high (tens of MeV) electron beam energies are used in order to obtain a sufficiently high neutron yield per original incident electron. The photoneutrons that are thus produced inherently have energies that are much too high for BNCT purposes. So much filtering would be required for these high-energy sources that sufficient neutron flux intensities within the required epithermal energy could not reasonably be obtained while simultaneously suppressing the higher than epithermal flux to a radiobiologically satisfactory level.

The use of a relatively low electron beam energy (8 to 12 MeV) was shown to offer a potentially-useful approach by a solely mathematical study conducted by two of the present applicants and published in abstract form in November 1992. This study was based on the contemplated use of an accelerator-based device capable of producing a filtered photoneutron beam having a flux intensity about 5 to 10 times lower than what we, in accordance with the present invention, now regard and what has historically been accepted in the relevant scientific community as the desired level (a minimum of $1.0 \times 10^9$ n/cm$^2$/sec) for practical BNCT.

Nothing in the known prior art suggests that such a minimum level of flux intensity for a delimited beam of epithermal neutrons can be obtained by use of an electron accelerator. This was not shown to be obtainable by the hereinbefore-referred-to, solely mathematical study published in November 1992 in abstract form, nor has it been known to be obtainable by any electron radiation impinged on photon producing target material. Moreover, the specific filtering and moderating materials, and the relative proportions thereof, have not been suggested, except as previously indicated with respect to nuclear-reactor based systems.

SUMMARY OF THE INVENTION

In the making of the present invention, it was a principal objective to produce, from an accelerator-based source or sources activated by what is regarded in the art concerned as low level electron beam energy, an epithermal neutron beam or beams having required spectral purity for effective and safe application of BNCT to a patient.

This has not been shown by any known prior art to have been accomplished heretofore and it is not believed to have been obvious to one skilled in the art at the time of the present invention.

We have now determined that, as indicated by the solely mathematical study previously referred to, the flux intensity of the filtered photoneutron beam of the above-mentioned published study was too low for practical application and had only some of the required spectral characteristics for epithermal neutron BNCT. Accordingly, we have now developed apparatus and procedures for achieving the foregoing objective of the invention.

The accelerator-based apparatus of the invention comprises target material having a high atomic number, e.g. metallic tungsten, in the form of thin plates (thickness limited to approximately one to five millimeters) arranged in close heat-exchange relationship with and along the outside surface of a tank or other container holding a photoneutron emitter that includes heavy water (deuterium oxide, $D_2O$) so as to transfer, to the heavy water, heat generated by the irradiation of such target plates with electrons impinged thereon. Such tank may contain up to approximately 50% by volume of beryllium in its internal construction. When beams of electrons having energies approximately in the range of 2 to 10 MeV impinge upon such target material, a significant portion of the energy of the impinging electrons is converted into bremsstrahlung photon radiation, which will be predominately directed into the tank and will be absorbed by the heavy water and by whatever metallic beryllium and/or other photoneutron emitter is incorporated therein to produce a strong, largely isotropic source of neutrons.

The neutrons so-generated have a characteristic photoneutron spectrum (as modified somewhat by neutron scattering interactions with the materials in the tank). They are passed as one or more beams into a filtering and moderating region of the apparatus. Attenuation to clinically-acceptable levels for BNCT application of both the direct bremsstrahlung radiation that is produced and of the neutron-capture gamma radiation that is generated throughout most regions of the apparatus, is effectively accomplished in customary manner by a heavy gamma shield (typically composed of bismuth and lead) that surrounds the apparatus, and by additional gamma-shielding materials placed at strategic locations within the apparatus. Geometric shaping of the final epithermal-neutron flux emerging from the gamma shield is accomplished by beam delimiting apertures, wedges, or other similar devices, typically composed of lithiated polyethylene or of similar neutron-thermalizing and neutron-absorbing material.

Besides the provision for circulating and cooling of heavy water from a body of photoneutron emitter that includes heavy water and that is surrounded by the target material, the accelerator-based apparatus of the invention provides for directing electron radiation radially onto target material that circumferentially encircles a cylindrical or spherical tank containing the heavy water, from a plurality of electron linear accelerators through usual drift tubes thereof and directing resulting beams of neutrons from the body of heavy water through a cylindrical or spherical filtering and moderating region that circumferentially surrounds the tank containing the body of photoneutron emitter that includes heavy water.

BRIEF DESCRIPTION OF THE DRAWINGS

The best mode presently contemplated for carrying out the invention in actual practice is illustrated in the accompanying drawings, in which.

DETAILED DESCRIPTION OF THE INVENTION

Figure 1:
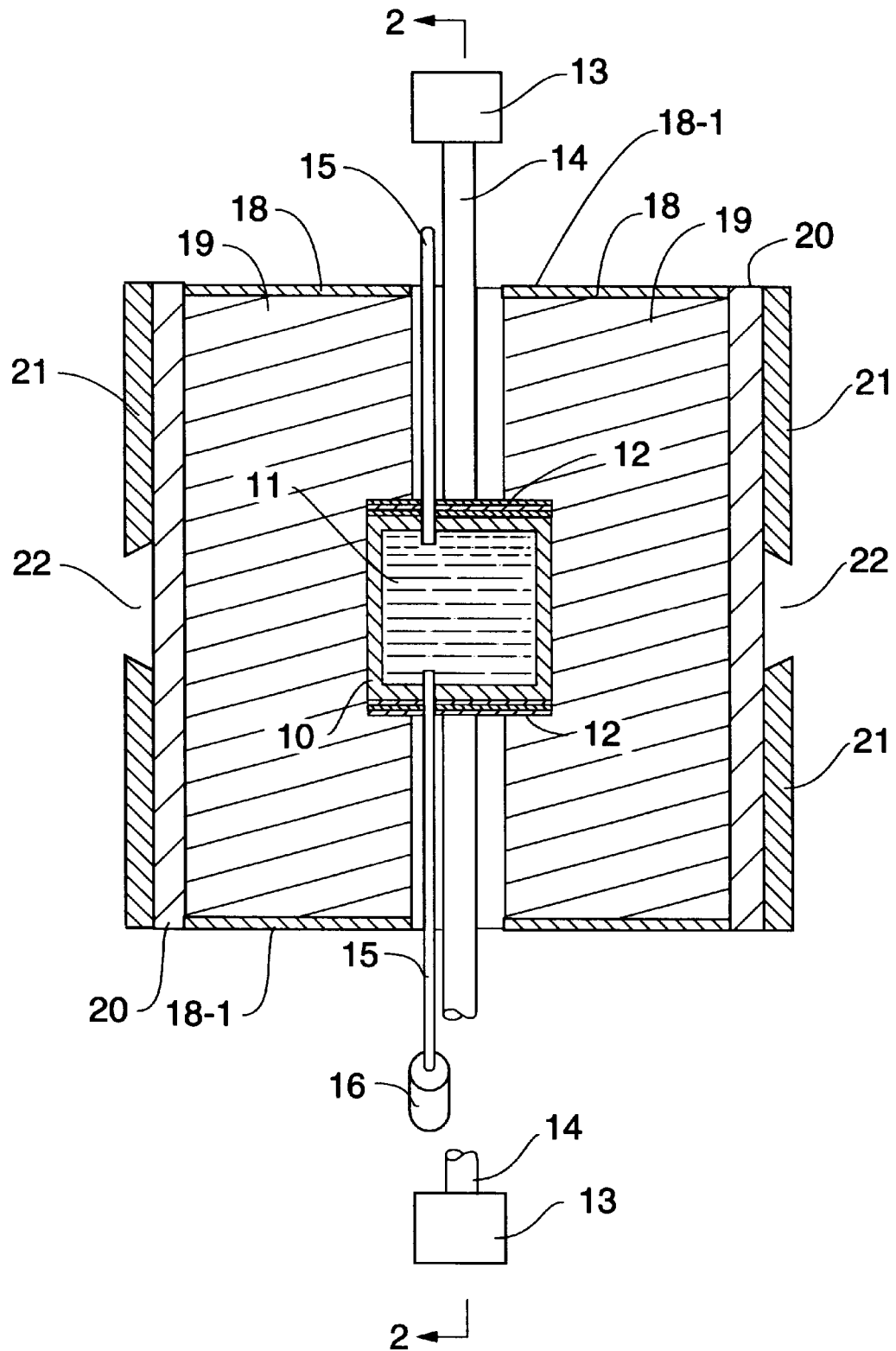
FIG. 1 is a schematic representation of a preferred embodiment of apparatus.
Figure 2:
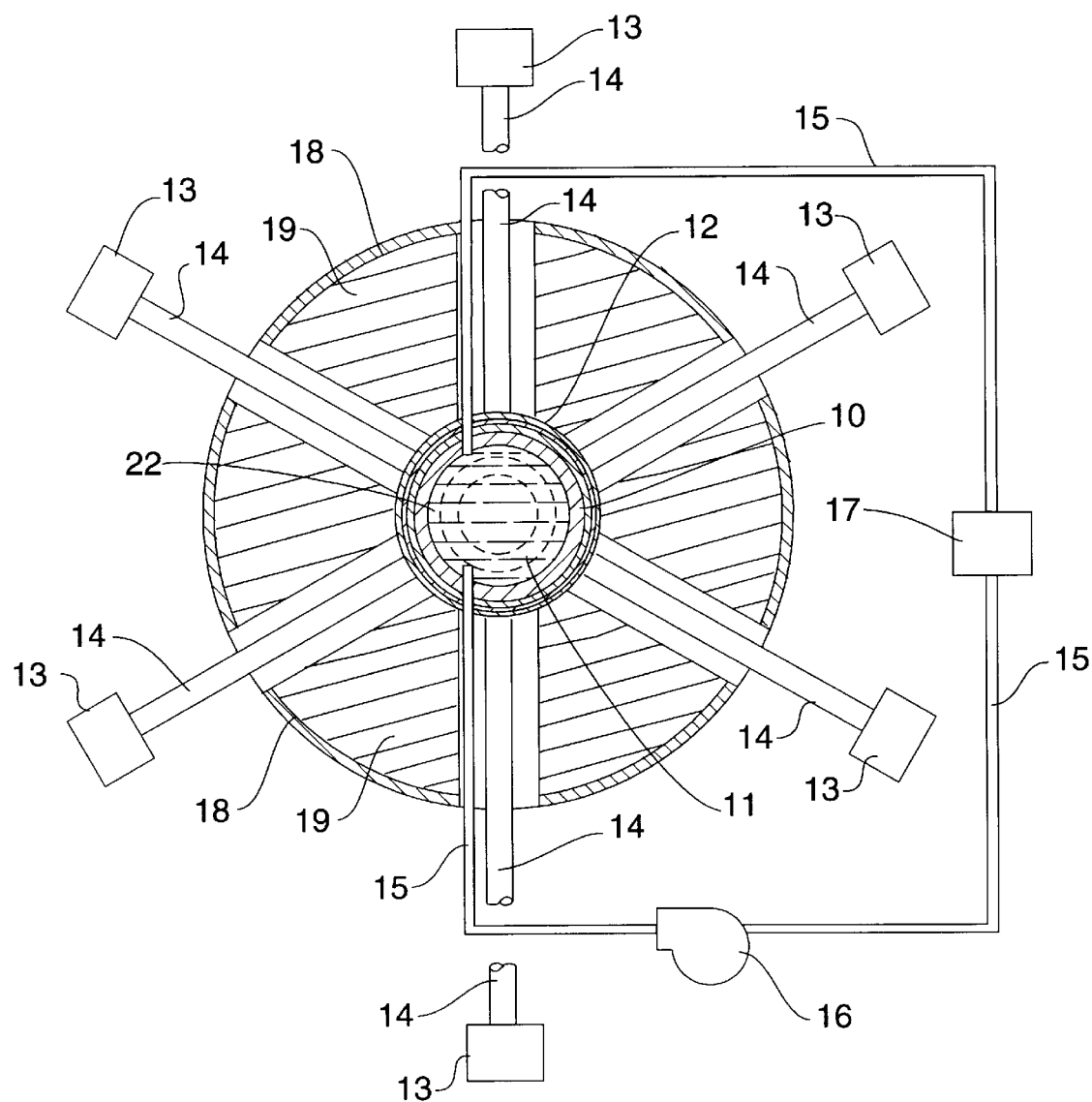
FIG. 2, an axial vertical section taken on the line 2—2 of FIG. 1.

As illustrated in FIGS. 1 and 2, largely schematically, a cylindrical aluminum tank 10 with a cylindrical wall 10a and opposite end walls 10b, respectively, has both a diameter and a length of typically 0.3 meters and contains a body 11 of photoneutron emitter that includes heavy water ($D_2O$). Circumferentially surrounding the outer cylindrical surface of tank 10 in close association therewith for heat transfer to the neutron emitter are a plurality of thin (typically one to five millimeters), cylindrical, target plates 12 intimately associated with one another and with tank 10 for the purpose of passing heat into the body 11 within the tank. Such tank 10 may include in its construction, or inwardly thereof, up to approximately fifty percent (50%) by volume of metallic beryllium; that which is not incorporated in the tank construction being intermixed heterogeneously with the heavy water.

Electron beams having a characteristic optimum energy of approximately 6 MeV, being above the approximately 2 MeV threshold for photoneutron production but below the energy that would result in the production of excessive direct bremsstrahlung radiation at the patient location (approximately 10–20 MeV) are directed radially of tank 10 at a number of locations, here six as shown in FIG. 2, onto the respective thin tungsten target plates 12 that surround the cylindrical wall 10a of tank 10. This is accomplished using standard electron linear accelerators 13 having drift tubes 14. The photon radiation is absorbed by the heavy water in, and by the beryllium of and in tank 10, resulting in the production of neutrons.

Removal of heat as produced in target plates 12 and passed into tank 10, as well as the relatively small amount originating in the heavy water and beryllium in the producing of photoneutrons, is accomplished by withdrawal of heavy water from tank 10 and circulating it through conduit means, here shown as a loop of piping 15, by circulator means such as a pump 16 connected into said loop of piping, and through cooling means 17, FIG. 2, (which may be an air-cooled heat exchanger that is also connected into said loop of piping 15) at a flow rate, e.g. 10–20 liters per second, such that the temperature of the heavy water is kept well below the boiling point during operation of the apparatus.

The neutrons produced isotopically within tank 10 enter a surrounding, cylindrical, filtering and moderating region 18, within which are neutron filtering and moderating materials 19 preferably selected from groups consisting of a group (1) a combination comprising metallic aluminum, lithiated aluminum, lithium fluoride to suppress thermal neutron flux, and aluminum trifluoride ($AlF_3$) in the proportions of approximately 0–30%, 0–30%, 0–5%, and 60%–100%, respectively, by volume, the lithiated aluminum containing from a trace of elemental lithium, to suppress thermal flux, up to approximately 3% by weight, a group (2) comprising a combination of lithiated metallic aluminum (lithium content as indicated above) and heavy water ($D_2O$) in the proportion of approximately 90% and 10%, respectively, by volume, and a group (3) comprising a combination of lithiated aluminum (lithium content as indicated above) and polymerized carbon difluoride ($CF_2$), the material Teflon®, in the proportions of approximately 50% each, by volume.

The metallic aluminum in the first group noted above is supplied, for example, either mixed homogeneously with the aluminum trifluoride, or in the form of hexagonal or other suitably-shaped aluminum canisters that contain aluminum trifluoride in crystalline form. The metallic aluminum in the second and third groups noted above may be supplied in the form of plates that are heterogeneously interspersed in laminated fashion within the heavy water or $CF_2$ in the filtering and moderating region 18.

At the ends of the cylindrical wall 18-1, that circumferentially defines filtering and moderating region 18 are end walls 20 in the form of bismuth and lead shields for attenuating gamma radiation, and next to such shields 20 are customary neutron beam delimiters 21, typically of lithiated polyethylene, having central openings 22. Desired epithermal beams pass through openings 22 providing the neutron spectra for patient irradiation.

It should be noted that gamma radiation produced both within the tungsten target plates 12 and from neutron capture throughout the apparatus is suppressed to clinically-acceptable levels. Additional gamma shielding may be placed at various strategic locations within the device as required to further facilitate suppression of the direct bremsstrahlung component of the radiation fields existing at the irradiation points.

Two horizontally-opposed, epithermal neutron beams for BNCT application to respective patients are produced by the illustrated apparatus for application to patients at the respective patient-irradiation positions 22, one of which may be plugged off in any suitable manner if not needed.

Although we prefer to use standard accelerator-based apparatus, as here schematically indicated, as the best mode presently contemplated for carrying out the invention, it is realized that other embodiments of such apparatus may be developed and used for the purpose. Also, other combinations of filtering and moderating materials 19 within region 18 are possible; a suitable quantity (not shown) of fissile material, e.g. uranium-235, clad in a protective material such as aluminum, may be included within or arranged around tank 10 to increase the net neutron yield of the device by the process commonly known as subcritical neutron multiplication; bremsstrahlung-producing electron accelerator targets other than tungsten may be employed; and beam delimiter apertures of various shapes and sizes may be used to tailor the beam geometry as deemed appropriate for each individual patient. Additionally, the photoneutron production devices and the filtering and moderating region 18 may be spherical as previously indicated.

Figure 3:
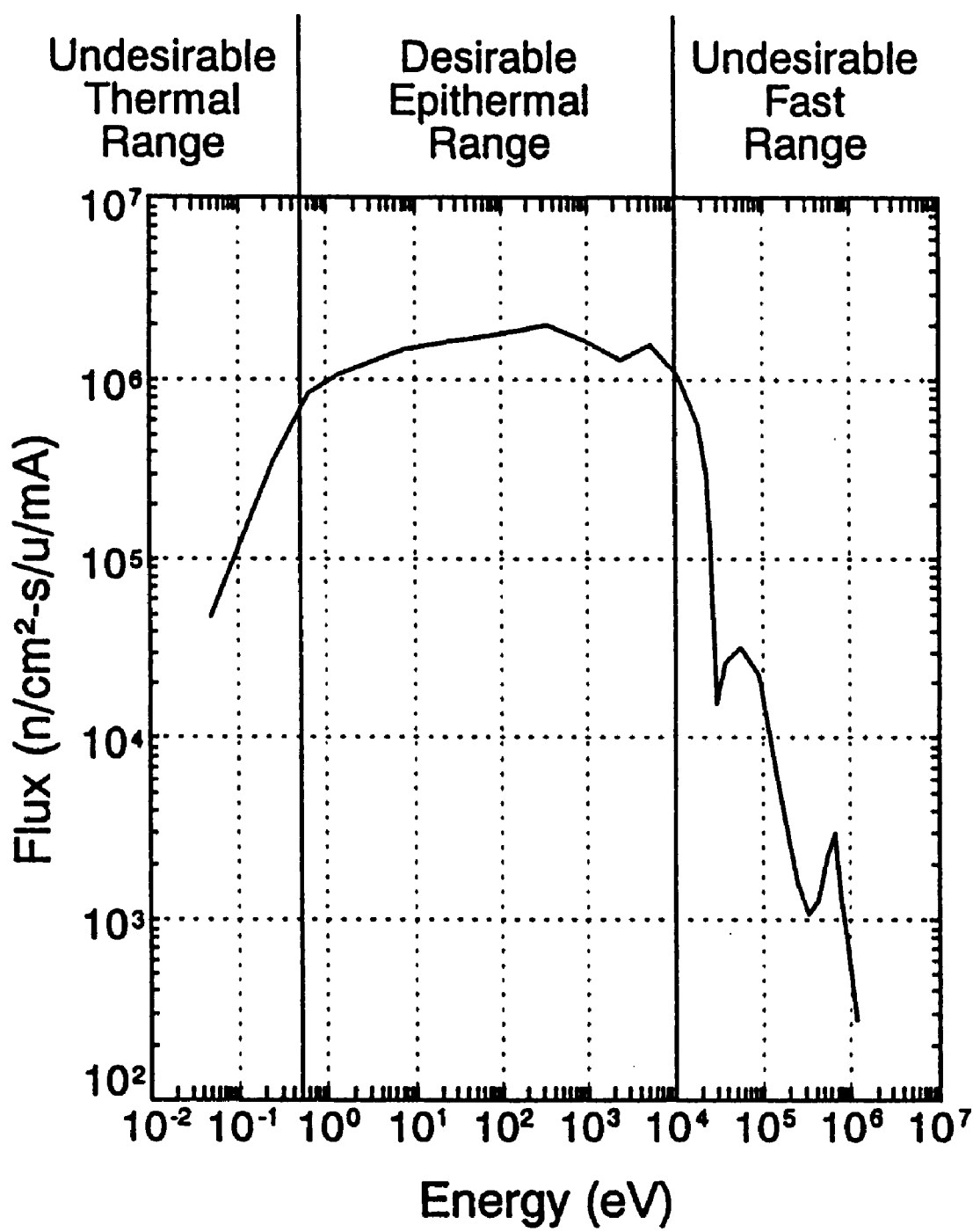
FIG. 3, a graph showing the intensity and spectrum of the emergent free-field neutron flux that is produced at patient locations by the apparatus of FIG. 1 per unit of incident electron beam current and per unit of neutron lethargy as calculated by generally-accepted methods.

The graph of FIG. 3 is based on the results of performance calculations based on sophisticated state of the art, multidimensional, stochastic simulation (Monte Carlo) and deterministic (Discrete-Ordinates) computational methods for radiation transport and interaction analysis. The computational methods employed for this purpose are commonly accepted in the relevant technical community. FIG. 2 shows the calculated scaler neutron flux intensity and spectrum at the irradiation positions 22 of FIG. 2 for the instance where lithiated aluminum and aluminum trifluoride are selected as the filtering and moderating materials 19 within the region 18. The results depicted in FIG. 3 show that an excellent, high-purity, epithermal neutron flux can be obtained at each of the patient irradiation positions 22.

As can be seen, the flux distribution exhibits high intensity in the desired epithermal energy range (0.5 to 10,000 eV) and the flux distribution above and below the desired energy range is suppressed to much lower levels. The total absolute intensity of the output neutron beams (i.e. the integral under the curve of FIG. 2) is in the range of $1.0 \times 10^7$ neutrons per square centimeter per second (n/cm$^2$/sec) per milliampere of impinging electron beam current. Thus, a clinically-useful neutron flux intensity of $1.0 \times 10^9$ n/cm$^9$/sec or thereabout can be attained using a total impinging electron beam current of 100 milliamperes with currently available electron linear accelerator technology. Intensities above this level can be achieved by increasing the electron beam current, should this be desired by the attending physician. Calculated results (not included in FIG. 3) show similar performance for the instance in which lithiated aluminum and heavy water are selected as the moderating and filtering materials 19 within region 18.

Experimental proof-of-principle testing for a low-current benchtop prototype of the epithermal photoneutron source concept has been initiated and significant preliminary results have been produced, as reported in the printed publication "INEL BNCT Research Program Annual Report for 1995", dated April 1996 and now obtainable from Lockheed Idaho Technologies Company which publication is incorporated herein and made a part hereof by reference.

Whereas this invention is here illustrated and described with specific reference to a certain embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A method of producing at least one delimited beam of epithermal neutrons for use in boron neutron capture therapy, comprising:

providing a target comprising a material that generates photons when an electron beam is impinged thereon;

positioning a body of photoneutron emitter comprising heavy water in sufficiently close association with said target to absorb heat energy and photons therefrom, said heavy water also being capable of generating neutrons when the photons are absorbed therein;

impinging electron radiation having energy of approximately 6 MeV radially onto said target to produce photons, whereby at least a portion of the photons produced generate neutrons within said body of photoneutron emitter;

circulating heavy water from said body thereof through cooling means and back into said body for removing heat absorbed from the irradiated target; and passing at least one beam of neutrons from said photoneutron emitter through neutron filtering and moderating materials, through neutron delimiting means, and through gamma ray attenuating means, to provide said at least one delimited beam of epithermal neutron, having a minimum flux intensity level of at least substantially $1.0 \times 10^9$ neutron per square centimeter per second.

2. A method in accordance with claim 1, wherein the step of positioning a body of photoneutron emitter is performed by placing said body in substantially cylindrical form having an elongate circumferential surface and two ends and placing it relative to the target so said target closely surrounds the circumferential surface of said body, whereby the electron radiation is impinged on said target radially thereof and of said circumferential surface; and wherein the at a least one beam of neutrons is extracted from at least one end of said body of liquid photoneutron emitter.

3. A method in accordance with claim 1, wherein the step of passing the at least one beam of neutrons through filtering and moderating material is performed with filtering and moderating materials selected from the groups consisting of a group (1) a combination comprising metallic aluminum, lithiated aluminum, containing from a trace to about 3% of elemental lithium, lithium fluoride, and aluminum trifluoride (AlF$_3$) in the proportions of approximately 0–30%, 0–30%, 0–5%, and 60%–100%, respectively, by volume; of a group (2) a combination comprising lithiated aluminum, containing from a trace to about 3% by weight of elemental lithium, and heavy water (D$_2$O) in the proportions of approximately 90% and 10%, respectively, by volume; and of a group (3) a combination comprising lithiated aluminum from a trace to about 3% by weight of elemental lithium, and carbon difluoride (CF$_3$), the material Teflon®, in the proportions of approximately 50% each by volume.

4. A method in accordance with claim 1, wherein the step of passing the at least one beam of said neutrons through filtering and moderating materials is performed with filtering and moderating materials comprising lithium, aluminum, and fluorine nuclei.

5. A method in accordance with claim 1, wherein the step of passing the at least one beam of said neutrons through filtering and moderating materials is performed with filtering and moderating materials comprising aluminum and fluorine nuclei.

* * * * *